(12) United States Patent
Wimberger-Friedl et al.

(10) Patent No.: US 8,618,508 B2
(45) Date of Patent: Dec. 31, 2013

(54) DETECTION SYSTEM AND METHOD

(75) Inventors: Reinhold Wimberger-Friedl, Eindhoven (NL); Jeroen Hans Nieuwenhuis, Eindhoven (NL); Johannes Joseph Hubertina Barbara Schleipen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 109 days.

(21) Appl. No.: 13/119,897

(22) PCT Filed: Sep. 21, 2009

(86) PCT No.: PCT/IB2009/054123
§ 371 (c)(1),
(2), (4) Date: Mar. 18, 2011

(87) PCT Pub. No.: WO2010/035204
PCT Pub. Date: Apr. 1, 2010

(65) Prior Publication Data
US 2011/0168918 A1    Jul. 14, 2011

(30) Foreign Application Priority Data

Sep. 25, 2008    (EP) .................................... 08165142

(51) Int. Cl.
*G01J 1/42*    (2006.01)
*G01J 1/58*    (2006.01)
*G21K 5/00*    (2006.01)

(52) U.S. Cl.
USPC ..................... 250/459.1; 250/458.1; 250/216

(58) Field of Classification Search
USPC ......... 250/361 R, 458.1, 459.1, 216; 436/172
See application file for complete search history.

(56) References Cited

U.S. PATENT DOCUMENTS

| 5,166,813 | A | 11/1992 | Metz | |
| 6,867,680 | B1 * | 3/2005 | Kulle | .......................... 338/32 H |
| 7,175,811 | B2 | 2/2007 | Bach | |
| 2006/0158659 | A1 * | 7/2006 | Colonna De Lega et al. | .............................. 356/497 |
| 2006/0216696 | A1 | 9/2006 | Goguen | |

(Continued)

FOREIGN PATENT DOCUMENTS

| JP | 06-289092 | * 10/1994 |
| JP | 09089774 | 4/1997 |

(Continued)

OTHER PUBLICATIONS

Wellman, Amber D. et al "Magnetically-Assisted Transport Evanescent Field Fluoroimmunoassay" Anal. Chem. 2006, vol. 78, pp. 4450-4456.

(Continued)

*Primary Examiner* — David Porta
*Assistant Examiner* — Abra Fein (57) ABSTRACT

A detection system combining an excitation radiation source providing excitation radiation to an analysis region of a sample within a substrate having a detection surface, a detector for detecting radiation collected from the analysis region comprising the detection surface of the sample resulting from the excitation, and a magnet arrangement beneath the analysis region of the sample, and stationary with respect to the excitation radiation source and light coupling arrangement, for attracting magnetic beads within the sample to the substrate surface. The detection radiation is collected from the detection surface of the substrate to give an enhanced surface specificity.

20 Claims, 5 Drawing Sheets

(56) References Cited

U.S. PATENT DOCUMENTS

| | | | |
|---|---|---|---|
| 2006/0274301 A1* | 12/2006 | Tuschel et al. | 356/73 |
| 2007/0041090 A1* | 2/2007 | Grafe et al. | 359/371 |
| 2007/0081163 A1 | 4/2007 | Liang | |
| 2011/0027916 A1* | 2/2011 | Nieuwenhuis | 436/526 |
| 2011/0062348 A1* | 3/2011 | Matthae et al. | 250/458.1 |

FOREIGN PATENT DOCUMENTS

| | | |
|---|---|---|
| JP | 2005077338 | 3/2005 |
| WO | 9203730 A1 | 3/1992 |
| WO | 9906503 A1 | 2/1999 |
| WO | 2007132373 A2 | 11/2007 |
| WO | 2008072156 A2 | 6/2008 |

OTHER PUBLICATIONS

Wellman, Amber D. et al "Multiplexed, Waveguide Approach to Magnetically Assisted Transport Evanescent Field Fluoroassays", Anal. Chem. 2007, vol. 79, pp. 6622-6628.

Morozov, Victor N. et al "Active Bead-Linked Immunoassay on Protein Microarrays" Analytica Chimica Acta, 2006, vol. 564, No. 1, pp. 40-52.

* cited by examiner

DETECTION SYSTEM AND METHOD

FIELD OF THE INVENTION

The invention relates to detection systems and methods, particularly in the field of diagnostics.

BACKGROUND OF THE INVENTION

One example of a detection system is based on creation of fluorescence radiation in a sample that may be detected to analyse the sample with respect to its constitution, and an example of the use of fluorescence detection is in nucleic acid testing (NAT). This is a core element in molecular diagnostics for detecting genetic predispositions for diseases, for determining RNA expression levels or identification of pathogens, like bacteria and viruses that cause infections. Such biosensing methods can also be used to detect other analytes such drugs (therapeutic or abuse) or markers for disease in bodily fluids such as for example blood, urine or saliva.

The detection of fluorescence can be used both for a qualitative or a quantitative determination of the presence of a particular target analyte in a sample (e.g. DNA, protein or drug. The present invention relates to the apparatus used to detect fluorescence, and the method of use.

Many examples of chemical or biological assay methods for specific binding, capturing and even isolating such targets using for example antibodies immobilised or not are generally known form handbooks such as for example Immunology 5th edition 1998 ISBN 0723429189 see for example chapters 6, 9 29). Often used in this respect are the so called competition and sandwich assays. In a typical molecular diagnostic experiment, a bio-sample is screened for detection of certain biological components (the "target"), such as genes or proteins, the latter often providing markers for specific diseases. This is done by detecting the occurrence of selective bindings (known as hybridisation) of the target to a capture probe, such as for example an antibody. The hybridisation step is typically followed by a washing step, where all unbound target molecules are flushed away, and finally a detection step is carried out. DNA, or RNA detection is generally performed using a replication phase performed before the detection. In this replication phase the DNA or RNA to be detected and present in only small amount within the sample is replicated to larger amounts in order to facilitate reliable detection. Since, the replication step is costly in time and energy, a low detection boundary is important. The apparatus of the invention is useful in that respect.

There are two general detection approaches: homogeneous tests (in solution), and heterogeneous tests (on a surface). Heterogeneous tests are more widespread for several reasons, the most important being the fact that they allow the use of special surface sensitive techniques which yield a more sensitive detection. The detection is based on fluorescent detection of fluorescent labels attached to the target molecules. The fluorescent detection needs to be very sensitive, and for heterogeneous tests, the detection must be surface specific so as to minimize the biological background. Ideally, the fluorescent detection needs to be capable of single fluorescent label detection, while the process is kept time effective.

The capture probes can be applied in a patterned fashion which allows multiplexing (i.e. detecting many different targets in parallel). The main disadvantages of such heterogeneous, i.e. surface immobilized capture immunoassays, is that the analytes need to diffuse and bind to the surface which usually is the rate limiting step in the analysis.

Magnetic beads with surface immobilized capture probes are used frequently to extract components such as the analytes referred to above, from a solution. The beads can be pulled towards the surface by external magnets. In a second step, the beads can be re-dispersed in the fresh solution by removing the magnetic attraction. The actuation force depends on the field strength and the magnetic volume of the bead.

Magnetic beads can also be used as labels. The sensitive detection of the presence of target molecules can either be based on the signal generated by the magnetic beads (either based on optical, electrical or magnetic properties) or a signal which is generated by any other label attached to the magnetic beads.

A currently implemented solution of magnetic actuation with optical detection is the detection of the attenuation of an excitation beam entering at an oblique angle

SUMMARY OF THE INVENTION

The inventors have recognized that in the currently implemented solution described here above a small change of a large signal needs to be detected which may have noise limitations. An improved sensitivity may be obtained from a detection of luminance emitted from the bound labels. For fast and efficient detection, which is mandatory in point-of-use applications, not only sensitive detection is important but also compact construction is of paramount importance as such devices must be handled in the field often in chaotic environment and/or by one person.

Thus there is a practical constructive limitation for the combination of improved optical read out and magnetic actuation when related to a device suitable for point of care use.

It is an object of the invention to provide a detection system that at least partly obviates the aforementioned problem.

The invention is defined by the independent claims. The dependent claims provide advantageous embodiments.

The arrangement according to the invention enables and makes use of magnetically activated displacement of captured targets towards a detection surface, selective excitation of these captured targets at the detection surface from and detection the response of the excitation in order to know the presence of the target. This surface localized excitation gives an enhanced surface specificity, so that a sensitivity enhancement in detection is achieved. The invention combines the advantages of surface detection with a simple low cost magnetic system for bringing the target to the surface. The magnetic system provides a high speed transport mechanism. In addition, both excitation and detection are done from one side of the detection surface so that a compact construction of the device is achieved. Accordingly, the device can be produced as a low cost compact arrangement by providing a fixed magnet and radiation guidance system. Magnetic actuation allows attracting beads towards (up-concentration) and away from (washing) the surface efficiently, while the dimensions of the beads ensure that strong radiation signals can be generated.

In an embodiment the excitation radiation is evanescent with the advantage to have increased selectivity of excitation at the detection surface. A magnetic field guide arrangement is preferably provided for focusing the magnetic field from the magnet to the analysis region. This enables the magnet to be located away from the analysis region, so that there is sufficient space for the magnet and the excitation source and detector.

The magnetic field guide arrangement can be arranged in a horse-shoe configuration (essentially a linear arrangement), with the collected radiation passing down the centre of the field guide to the detector. This provides a compact arrangement. The radiation coupling arrangement can then provide the excitation radiation to the analysis region up the central opening of the horse-shoe field guide arrangement, and has a radiation coupling arrangement for focusing the radiation onto the analysis region to generate the evanescent radiation in the sample. The radiation coupling arrangement can then also be for focusing the collected radiation to the detector, and the radiation coupling arrangement can comprise a beam-splitter for providing different radiation paths for the collected radiation and the excitation radiation. This provides a compact combined excitation and detection radiation system, partly housed within the centre of the annular magnetic field guide.

The detector can instead be mounted at the top surface of the magnet arrangement.

The detector and the magnet arrangement can instead be side by side on a carrier, and wherein the carrier is movable between a magnetic actuation position and a detection position. This can improve the image quality. The actuator will need to be scanned only a small number of times during an assay.

Generally, the detector preferably comprises a radiation focusing arrangement. In one arrangement, the radiation focusing arrangement comprises a radiation guide.

The detector can comprise a radiation band pass or high pass filter, to remove background noise from the detected radiation signal.

In another arrangement, the radiation coupling arrangement comprises a radiation coupling arrangement associated with the excitation radiation source for directing the excitation radiation to the analysis region at an acute angle with respect to the detection surface or, if that is parallel to the substrate surface, parallel to the substrate surface, such that the detection surface provides total internal reflection. This total internal reflection provides the evanescent wave in the sample. The acute angle means that the radiation paths close to the analysis region do not occupy a large depth, so that the magnet can be kept close to the analysis region. The detection is effectively confined to a thin layer above the detection surface.

In another arrangement, the radiation coupling arrangement comprises an evanescent radiation guide at the detection surface which is in contact with the sample, again confining excitation to a very thin layer of the sample near or at the detection surface. The excitation radiation may be coupled into this waveguide at a distance from the detection surface and hence from the magnet and radiation coupling equipment/and/or detector so that they do not have to interfere with each other with respect to space available in the device. A compact device is enabled having the advantageous of sensitive measurement at the surface using the magnetic actuation.

In another arrangement, the radiation coupling arrangement generates a non-evanescent, travelling wave confined in a shallow volume close to the surface which is in contact with the sample This is known as "double refraction detection". The shallow volume can have a depth of several to tens of microns.

The detection and/or excitation radiation may be optical radiation including or excluding near infrared radiation and/or UV radiation. The interaction of the sample with the excitation radiation may include reflection, absorption or luminescence, where luminescence includes phosphorescence and/or fluorescence. Preferably the excitation radiation is optical radiation while the detection radiation is luminescence radiation as that provides increased sensitivity. Most preferably the detection radiation is fluorescence radiation which provides extremely sensitive detection.

In cases where the method relies on absorption of excitation radiation followed by the emittance of the converted excitation radiation such as for example in luminescence generation, the sample may be provided with suitable species for conversion.

The detector may comprise a pixilated radiation detector. The system preferably comprises a biological component screening system, for screening for a particular analyte such as for example a protein, drug, DNA, RNA or other molecule.

The combination of detection of fluorescence light and the use of magnetic actuation is known per se (Anal. Chim. Acta 564, 2006, 40). However, the solution disclosed is not compact in the sense of the present invention.

BRIEF DESCRIPTION OF THE DRAWINGS

Examples of the invention will now be described in detail with reference to the accompanying drawings, in which.

The same reference numbers are used to denote the same components in different Figs. When a Fig. includes the same components as a previous Fig., the description is not repeated. Where reference numbers are used in the claims, this is only to assist in an understanding of the invention and is not intended to limit the scope of the claims.

DETAILED DESCRIPTION OF EMBODIMENTS

The invention relates to an optical analysis apparatus and method which combines surface localized excitation with magnetic bead capture. Making use of surface localized excitation gives an enhanced surface specificity, so that a selectivity enhancement in fluorescence detection is achieved. The magnetic bead capture provides a low cost and compact way of enabling surface measurement, with high speed movement of particles to the surface.

One way to achieve surface localized excitation is to use evanescent excitation. The principle of evanescent excitation will first be explained with reference to FIG. 1.

Figure 1:
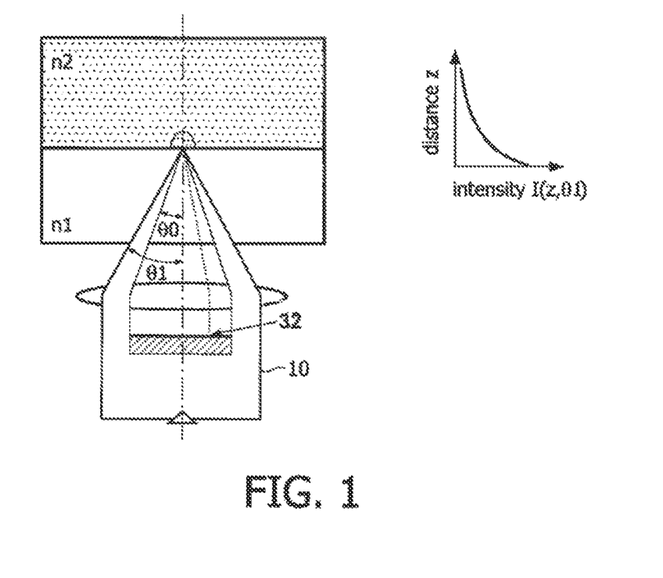
FIG. 1 is used to illustrate the principle of evanescent excitation.

The sample 14 to be investigated is confined into a given volume forming a micro-fluidic part by a substrate 16. A light source 18 directs excitation light 10 to the surface of the substrate 16.

By providing an angle of incidence of this excitation light larger than the critical angle, there is total internal reflection of the light. This removes the bulk excitation. An evanescent wave travels into the sample, with a decaying field amplitude as a function of propagation distance z, as schematically illustrated by plot 21. Since this evanescent wave is rapidly decaying, it can be used to probe only those molecules that are present near the surface of the interface.

Upon excitation with a (short wavelength) laser, the fluorescent molecules will start radiating light in all directions. The wavelength of the fluorescent light will be longer than the excitation wavelength.

Figure 2:
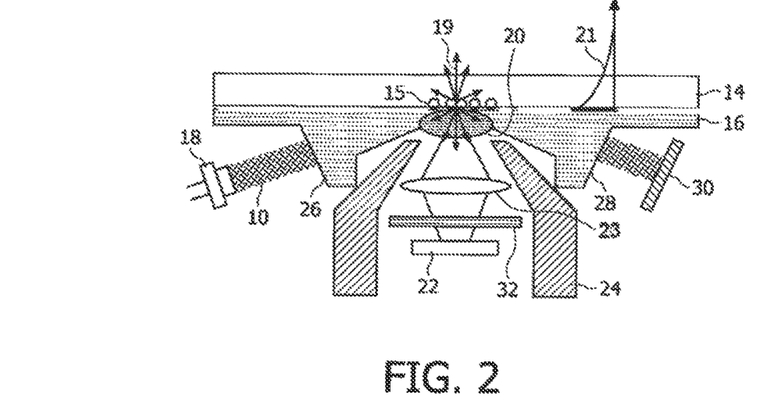
FIG. 2 shows a first example of analysis apparatus of the invention.

FIG. 2 shows a first example of device of the invention.

Generally, the device comprises a reader instrument and a disposable cartridge. The reader instrument has a magnet arrangement for bringing the magnetic beads to the surface and pulling them away from the surface, an optical excitation system for inducing fluorescence, and an optical detector.

As explained with reference to FIG. 1, the sample 14 to be investigated is confined into a given volume forming a microfluidic part by a substrate 16. The sample includes magnetic beads 15. Excitation light 10 generated by a source such as a laser (or LED) 18 is used to excite fluorescence 19.

The induced florescence emitted by the bound labels, (as a result of the evanescent excitation light provided into the sample) is collected by a collection lens arrangement 20, and is directed towards a detector 22. The detector is a photodetector, which can be a diode or an array of diodes or charge-coupled devices (CCD). The amount of light which reaches the sensor surface can be further increased by introducing optical elements such as lenses between the disposable part of the device (the substrate) and the detector 22. As shown in FIG. 2, the disposable substrate can also include optical surfaces 26, 28 defining part of the optics 23.

To reduce a background signal from scattering light, a color selective filter 32 (bandpass or highpass; where "high" refers to the wavelength of the light) is provided on top of the detector. The filter can be absorbing or reflecting (dichroic), and can be in optical contact with the detector.

The optical elements 20 can also be used to image the binding surface on the detector surface. In this way, a spatial image of the emitted light is created which allows simultaneous detection of different targets on different spots at the binding surface. This represents a multiplexed detection scheme.

The magnetic field for the magnetic bead capture is guided towards the bottom of the optical substrate 16 by using high permeability material forming guides 24. The magnetic field needs to be provided close to the binding surface of the optical substrate, in order to achieve sufficiently large forces (typically <1.5 mm between the top of the magnet and the substrate sensor area). The electromagnetic sources themselves are located at a larger distance, not shown in FIG. 2. This creates sufficient space between the magnetic field guides 24 to position the optical detection system. In the example shown, the guides form an horse-shoe shaped ring, and the central opening is used for housing the detection optical components. A large optical aperture of the magnetic guiding structure is desired for an increased light collection. The opening angle of the cone of light that has to be collected by the imaging optics should be large, for example corresponding to a numerical aperture of 0.5 of more.

The excitation light 10 enters the substrate 16 via window 26 which is integrated in the disposable part of the device. An exit window 28 is also shown, and an optional detector 30 used for feedback control of the excitation source, for example for reference and quality control.

In the example of FIG. 2, the excitation is achieved with an incident beam which is totally reflected at the interface between the substrate and the analyte solution at the spot of the biological binding. This creates the desired evanescent field at the surface with exponentially decaying intensity. Only labels in proximity of the surface (distance order of 100 nm or less) will become excited. Such a surface selective excitation creates a very low background from the supernatant solution and consequently allows real-time detection with high sensitivity. By providing the excitation source and associated lenses laterally of the analysis region of the sample, and with a small acute angle between the direction of incidence and the plane of the substrate, a small space can be provided between the magnetic field guides and the lower surface of the substrate.

In the arrangement of FIG. 2, the detector and associate optics are provided within a space at least partially surrounded by the magnetic field guides.

Figure 3:
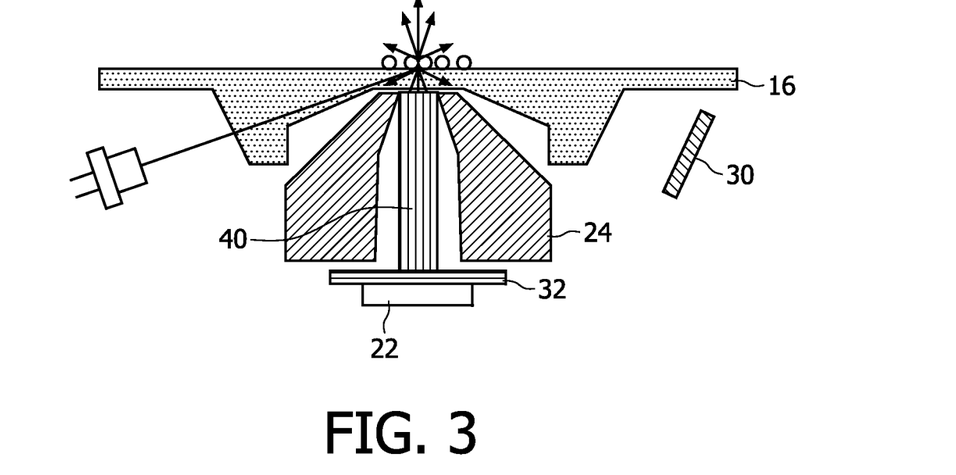
FIG. 3 shows a second example of analysis apparatus of the invention.

In a second embodiment shown in FIG. 3, the emitted light is transported from the analysis region by a light guide 40, for example fibre bundles. The detector 22 is placed at the lower end of the light guide 40 outside the magnetic head. This enables a more compact design of the magnetic field guides and allows the use of standard components for the optical elements.

Figure 4:
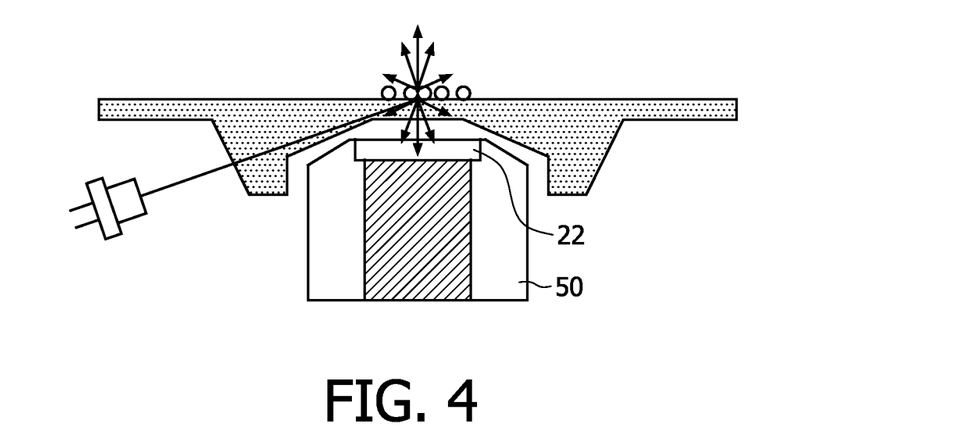
FIG. 4 shows a third example of analysis apparatus of the invention.

In a third embodiment shown in FIG. 4, the photodetector 22 is positioned directly on top of the magnet 50 that is used for actuation of the magnetic labels. The photodetector 22 is still however located in the reader instrument to keep costs of the disposable part of the apparatus low. FIG. 4 shows a flat underside of the substrate in the analysis region, but an optical component such as a single refractive or diffractive lens, or a 1D- or 2D-lenslet array (providing imaging functionality), could again be moulded in the bottom of the optical substrate to increase the collection efficiency, as shown in FIG. 2.

To keep the photodetector slim, it is preferably a semiconductor element (e.g. photodiode, CCD, CMOS) or a polymeric element.

Figure 5:
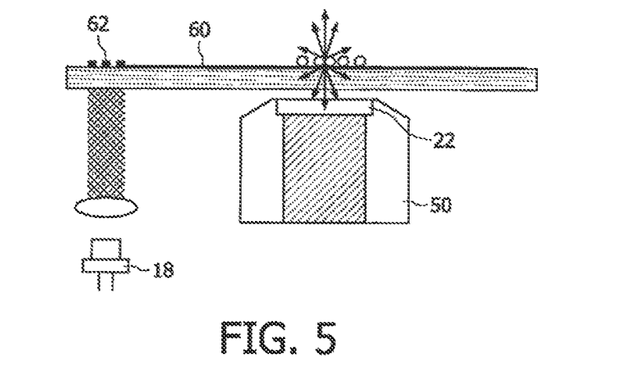
FIG. 5 shows a fourth example of analysis apparatus of the invention.

Excitation by total internal reflection as shown in the examples above can be replaced by excitation with an evanescent light guide, as shown in FIG. 5. In this way, no components are required at the location of the analysis region for coupling the light to the analysis region. This leaves more area for the magnetic head.

The excitation source 18 provides light to the light guide 60 by means of a grating structure 62.

Figure 6:
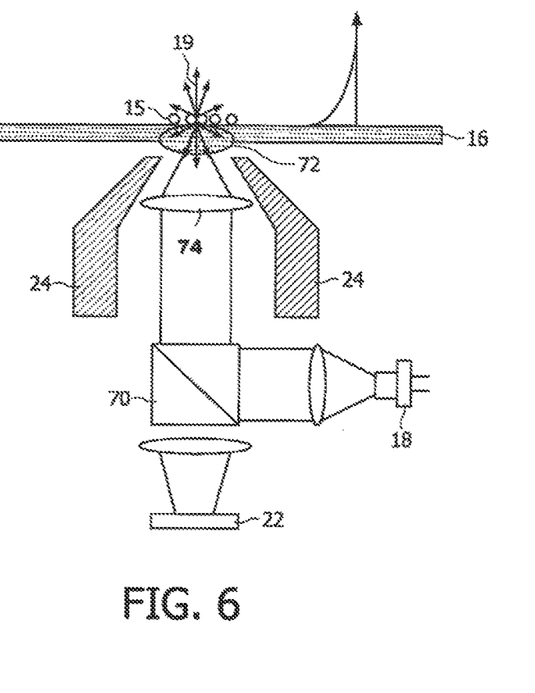
FIG. 6 shows a fifth example of analysis apparatus of the invention.

FIG. 6 shows an arrangement in which the excitation light is guided through the optical elements inside the magnetic head. In this way, an optical arrangement is used which provides the excitation light to the analysis region up the centre of the field guide arrangement (for example again in a horse shoe configuration). The light is focused onto the analysis region to generate the radiation in the sample.

The excitation light is directed to the sample by a dichroic mirror or beamsplitter 70. This enables different optical paths to be defined for the excitation lights and the fluorescence. The excitation light is subsequently focused in the sample by means of an excitation lens 72.

Any reflected stray laser light (having the excitation wavelength) is reflected again by the dichroic mirror or beam splitter 70, whereas the fluorescence luminance is passed through the mirror/beam splitter 70 to the detector 22.

A band pass filter can provide further filtering for rejection of the excitation light, and the filtered light is focused on the detector 22 by an imaging lens 74 which images the sample onto the detector 22.

The read-out can be implemented in a quasi-confocal mode by introducing a pinhole in the focal point of the collecting lens in the read out path or using the pixelated detector as a quasi-pinhole to suppress luminance from other parts outside the binding array. However, no pinhole arrangement is required when an evanescent field is present only at an excitation spot.

The examples above have fixed magnetic and optical components, and the magnetic and optical functions are performed with the same cartridge position.

Figure 7A:
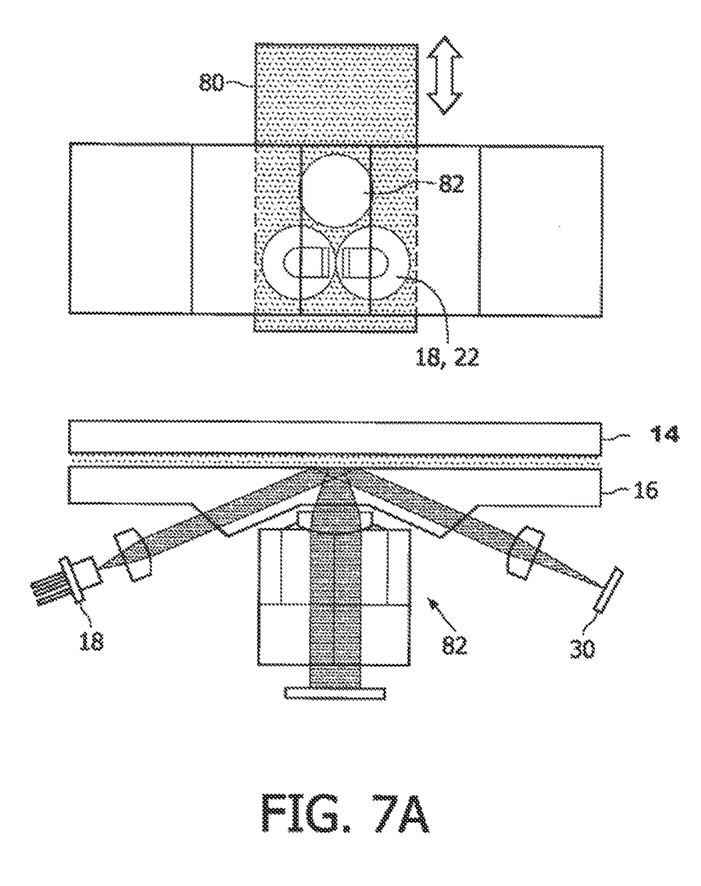
FIGS. 7A and 7B show a sixth example of analysis apparatus of the invention.
Figure 7B:
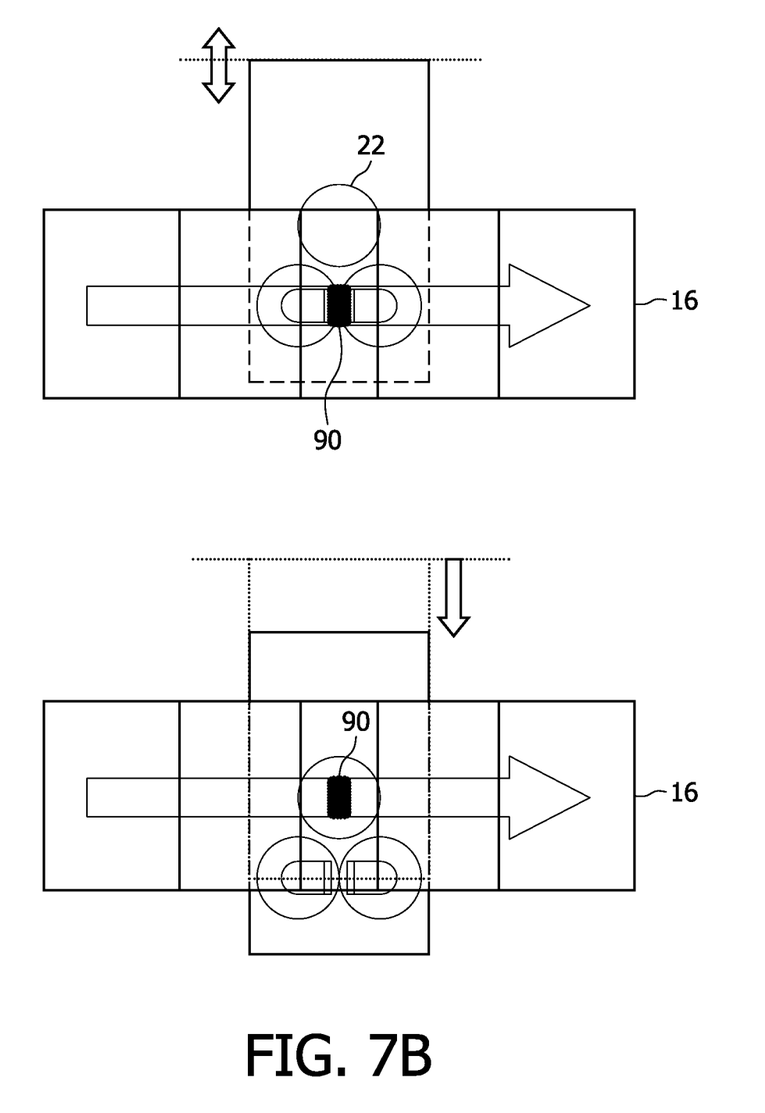

In an arrangement shown in FIG. 7, the coaxial arrangement of magnetic and optical elements replaced with a parallel arrangement with the advantage of having a better imaging quality. The arrangement of FIG. 7 has an actuated sledge 80 containing the magnet arrangement 82 and the imaging and detection optics 18, 22, next to each other.

FIG. 7A shows the device in side view and top view. FIG. 7B shows the two positions of the sledge 80. The top part of FIG. 7B shows the analysis region 90 in the path of the excitation source and above the magnetic field. The bottom part of FIG. 7B shows the analysis region over the optical detector arrangement for detecting the fluorescence.

The excitation of fluorescence, and light detection are at the same time (the relaxation time of fluorescence is a few nanoseconds). The arrangement of FIG. 7 separates the magnetic attraction function from the excitation/detection. The magnetic attraction is a comparatively slow process and once the beads are bound they remain in place sufficiently for the cartridge movement.

This arrangement uses the same conceptual approach as the examples of FIGS. 2 and 3, in that imaging of the analysis region is through the center of the magnet.

The example of FIG. 7 provides movement of the sledge 80 during actuation between two positions. A position is provided in which the magnet is exactly below the analysis region of the cartridge. When the actuation protocol has ended (magnetic attraction to bring particles to the surface), the sledge is moved to a second position such that the optical axis of the imaging/detection optics coincides with the center of the analysis region and excitation and fluorescence detection can take place.

In all examples above, the target molecules attach to the beads (in the same way as in existing bead capture systems), and the fluorescent labels attach to the target molecules (in the same way as in existing optical systems), so that magnetically drawing the beads to the surface provides the required fluorescent labels at the surface. Beads which are attracted to the surface but have no attached target molecule will not bind and can be pushed away by reversing the magnetic gradients.

The technology of 1D and 2D moving mechanical stages is well-known from optical storage and these devices can be made reliably, at low-cost and in high volumes. Furthermore, 1D actuated sledges can be moved fast (up to 100 Hz) and with high accuracy (tens of microns).

A possible disadvantage of this method is the lack of signal during magnetic actuation. However, for an end-user product this would be no problem since the dynamics of the bio-assay is known from research. The actuation protocol can thus be performed without requiring feedback or analysis.

The various examples of the invention enable a system with compact imaging optics and detector, and with high image quality. A compact and efficient magnet arrangement is provided.

The supply of the sample to the analysis region can be entirely conventional, for example using microfluidic pumping. Multiple channels can be in parallel with different antibodies immobilized.

Temperature control of the device can be provided by integrated heating. Fluorescent beads of different spectrum can be used.

The background fluorescence can be read from unbound labels. The background will result mainly from unintentionally bound labels and other particles that stick to the surface, as well as some intrinsic fluorescence from the substrate and all components in the light path.

Measuring the density of beads by absorption (FTIR) or scattering is an alternative which can be measured instead of or in addition to fluorescence. This can use essentially the same arrangement except the filters.

Premixing of the beads and labelled antibodies with the sample can take place before injection. Preferably, the mixing and reaction would take place inside the disposable cartridge for a point of care application.

In the examples above, the system is used for fluorescence detection. However, the invention more generally relates more generally to the excitation of a sample and the detection of resulting light.

The substrate may be a flat plate of any suitable material, e.g. may be of glass or a polymer, and may have capture elements with a surface density between 0.01 and 106 elements per $\mu m^2$, preferably between 10 and 104 elements per $\mu m^2$.

The sample, the substrate with capture elements in contact with the sample or the substrate after it has been in contact with the sample, typically is screened for certain components, e.g. biological components such as oligonucleotides, DNA, RNA, genes, proteins, carbohydrates, lipids, cells, cell components such as external cell membranes or internal cell membranes, bacteria, viruses, protozoa, etc. also called the target particles.

Luminescent labels typically are attached to the target particles and thus assist in the detection of target particles. In some embodiments the sample thus includes at least one luminescent label, also referred to as an "optically variable particle". Such optically variable particles can be, for instance, fluorescent (as described above), electroluminescent or chemiluminescent particles. The optical variable particles may be any entity that is capable to bind to a binding site chemically or otherwise. The binding is due to screening effects (i.e. ionic, dispersive and hydrogen bonding interactions). Covalent bonding is an alternative In the examples above, the fluorescence detection takes place through the substrate. However, the fluorescence detection can be implemented above the sample.

The applications of the invention are generally in the field of molecular diagnostics: clinical diagnostics, point-of-care diagnostics, advanced bio-molecular diagnostic research—biosensors, gene and protein expression arrays, environmental sensors, food quality sensors, etc.

Various other modifications will be apparent to those skilled in the art.

The invention claimed is:

1. A detection system comprising:
a substrate having a detection surface for holding a sample and including an excitation region at least partly in contact with the sample, and a radiation coupling arrangement for advancing excitation radiation from an excitation radiation source to the citation region to interact with bound labels of the sample to produce light coming from the bound labels;
a collection arrangement positioned in the excitation region for collecting and directing the light coming from the bound labels;
a detector for detecting the collected light; and
a magnet arrangement configured to be disposed next to and at the same side of the detection surface, to be stationary with respect to the excitation radiation source and the radiation coupling arrangement, and to attract magnetic beads within the sample to the detection surface.

2. The detector system as claimed in claim 1, wherein the excitation radiation is evanescent.

3. The detection system as claimed in claim 1, further comprising a magnetic field guide arrangement for focusing the magnetic field from the magnet arrangement to the excitation region.

4. The detection sterna claimed in claim 3, wherein the magnetic field guide arrangement comprises an opening through which the radiation coupling arrangement guides the excitation radiation and/or the light coming from the bound labels.

5. The detection system as claimed in claim 4, wherein the radiation coupling arrangement is configured to advance the excitation radiation to the excitation region up a center of the field guide arrangement.

6. The detection system as claimed in claim 5, further comprising a beam splitter for providing different radiation paths for the light coming from the bound labels and the excitation radiation.

7. The detection system as claimed in claim 1, wherein the detector is mounted on the surface of the magnet arrangement that is closest to the sample holder.

8. The detection system as claimed in claim 1, further comprising a carrier movable between a magnetic actuation position and a detection position,
wherein the detector and the magnet arrangement are mounted side by side on the carrier.

9. The detection system as claimed in claim 1, wherein the detector comprises a radiation focusing arrangement.

10. The detection system as claimed in claim 1, wherein the detector comprises one of a radiation band pass and high pass filter.

11. The detection system as claimed in claim 1, wherein the radiation coupling arrangement comprises a radiation arrangement associated with the excitation radiation source for directing the excitation radiation to the excitation region at an acute angle with respect to the detection surface of the substrate, such that the substrate provides total internal reflection.

12. The detection system as claimed in claim 1, wherein the radiation coupling arrangement comprises an evanescent radiation guide.

13. The detection system as claimed in claim 1, wherein the excitation radiation is light and the collected light is luminescence radiation.

14. The detection system as claimed in claim 1, wherein the detector comprises a pixelated light detector.

15. The detection system as claim in claim 1, wherein the excitation radiation source a light emitting diode (LED) and the collected light is scattered light.

16. A detection method comprising acts of:
disposing a magnet arrangement next to and at the same side of a detection surface of a substrate, the detection surface holding a sample and including an excitation region at least partly in contact with the sample;
advancing excitation radiation from an excitation radiation source to the excitation region using a radiation coupling arrangement to interact with bound labels of the sample producing light coming from the bound labels;
collecting and directing radiation of the light coming from the bound labels using a collection arrangement positioned in the excitation region; and
detecting the collected light coming from the bound labels.

17. The method as claimed in claim 16, comprising an act of mounting the detector on the surface of the magnet arrangement that is closest to the sample holder.

18. The method as claimed in claim 16, comprising acts of:
providing a carrier movable between a magnetic actuation position and a detection position; and
mounting the detector end the magnet arrangement side by side on the carrier.

19. A detection system comprising:
a substrate having a detection surface for holding a sample and including an excitation region in contact with the sample, and a radiation coupling configured to advance excitation radiation from an excitation radiation source to the excitation region to interact with bound labels of the sample to produce light coming from the bound labels;
a collector positioned in the excitation region configured to collect and direct the light coming from the bound labels;
a magnet arrangement configured to be disposed next to and at the same side of the detection surface, to be stationary with respect to the excitation radiation source and the radiation coupling arrangement, and to attract magnetic beads within the sample to the detection surface; and
a detector, configured to detect the light coming from the bound labels, mounted on the surface of the magnet arrangement that is closest to the sample holder.

20. The detection system as claimed in claim 19, further comprising a carrier movable between a magnetic actuation position and a detection position,
wherein the detector and the magnet arrangement are mounted side by side on the carrier.

* * * * *